United States Patent [19]
Wallach et al.

[11] Patent Number: 6,083,534
[45] Date of Patent: Jul. 4, 2000

[54] PHARMACEUTICAL COMPOSITIONS FOR CONTROLLED RELEASE OF SOLUBLE RECEPTORS

[75] Inventors: David Wallach, Rehovot; Josef Kost, Omer; Rom Eliaz, Beer-Sheva, all of Israel

[73] Assignees: Yeda Research and Development Co. Ltd., Rehovot; Ben-Gurion University of the Negev, Beer-Sheva, both of Israel

[21] Appl. No.: 08/894,913

[22] PCT Filed: Mar. 1, 1996

[86] PCT No.: PCT/US96/03121

§ 371 Date: Oct. 9, 1997

§ 102(e) Date: Oct. 9, 1997

[87] PCT Pub. No.: WO96/26738

PCT Pub. Date: Sep. 6, 1996

[30] Foreign Application Priority Data

Mar. 1, 1995 [IL] Israel ......................................... 112834

[51] Int. Cl.[7] ..................................................... A61K 9/16
[52] U.S. Cl. ........................... 424/484; 424/486; 424/487; 424/488; 424/405; 424/406; 424/417; 424/422; 424/423; 424/85.1; 424/85.4; 424/85.6; 424/158.1; 530/351; 514/12; 514/803; 514/825; 514/885; 514/889; 514/903; 514/921; 514/974
[58] Field of Search ...................................... 424/405, 406, 424/409, 417, 420, 158.1, 174.1, 177.1, 85.1, 85.6; 530/351; 514/12, 803, 825, 885, 889, 921, 974, 903

[56] References Cited

U.S. PATENT DOCUMENTS

| | | |
|---|---|---|
| 4,883,666 | 11/1989 | Sable et al. . |
| 4,929,442 | 5/1990 | Powell . |
| 5,013,556 | 5/1991 | Woodle et al. ........................ 424/400 |
| 5,206,023 | 4/1993 | Hunziker ................................ 424/423 |
| 5,324,519 | 6/1994 | Dunn et al. ............................. 424/426 |
| 5,470,582 | 11/1995 | Supersaxo et al. . |
| 5,478,564 | 12/1995 | Wander et al. ......................... 424/426 |
| 5,478,925 | 12/1995 | Wallach et al. ........................ 530/351 |

OTHER PUBLICATIONS

R. Eliaz et al., "Long–Term Protection Against the Effects of Tumour Necrosis Factor by Controlled Delivery of the Soluble p55 TNF Receptor", Cytokine, vol. 8, No. 6, pp. 482–487, Jun., 1996.

D. Aderka et al., "Increased Serum Levels of Soluble Receptors for Tumor Necrosis Factor in Cancer Patients" Cancer Research, vol. 51, pp. 5602–5607, Oct. 15, 1991.

D. Aderka et al., "Stabilization of the Bioactivity of Tumor Necrosis Factor by Its Soluble Receptors", J. Exp. Med., vol. 175, pp. 323–329, Feb., 1992.

H. Engelmann et al., "A Tumor Necrosis Factor–Binding Protein Purified to Homogeneity from Human Urine Protects Cells from Tumor Necrosis Factor Toxicity", J. Biol. Chem., vol. 264, No. 20, pp. 11974–11980, Jul. 15, 1989.

H. Engelmann et al., "Two Tumor Necrosis Factor–Binding Proteins Purified from Human Urine", J. Biol. Chem., vol. 265, No. 3, pp. 1531–1536, Jan. 25, 1990.

J.H. Korn et al., "Cloning of Genomic DNA for Tumor Necrosis Factor and Efficient Expression in CHO Cells", Lymphokine Research, vol. 7, No. 4, pp. 349–358, 1988.

(List continued on next page.)

*Primary Examiner*—Neil S. Levy
*Attorney, Agent, or Firm*—Browdy and Neimark, PLLC

[57] ABSTRACT

A controlled release pharmaceutical composition includes a biocompatible polymeric material, preferably polyethylene-vinyl acetate or poly(lactic-glucolic acid), having incorporated therein a soluble receptor capable of binding to its ligand and thus affecting the ligand's function. The soluble receptor is preferably the soluble form of TNFα receptor. Such compositions are for use in the treatment of disorders in which neutralization of the deleterious effects of TNFα is required.

34 Claims, 7 Drawing Sheets

OTHER PUBLICATIONS

R. Langer, "New Methods of Drug Delivery", Science, vol. 249, pp. 1527–1533, Sep. 28, 1990.

H. Loetscher et al., "Molecular Cloning and Expression of the Human 55 kd Tumor Necrosis Factor Receptor", Cell, vol. 61, pp. 351–359, Apr. 20, 1990.

Y. Nophar et al., "Soluble Forms of Tumor Necrosis Factor Receptors (TNF–Rs). The cDNA for the type I TNF–R, Clone Using Amino Acid Sequence Data of its Soluble Form, Encodes both the Cell Surface and a Soluble Form of the Receptor", The EMBO Journal, vol. 9, No. 10, pp. 3269–3278, 1990.

A. Oliff et al., "Tumor Secreting Human TNF/Cachectin Induce Cachexia in Mice", Cell, vol. 50, pp. 555–563, Aug. 14, 1987.

I. Olsson et al., "Isolation and Characterization of a Tumor Necrosis Factor Binding Protein From Urine", Eur. J. Haematol., vol. 42, pp. 270–275, 1989.

L. Probert et al., "Wasting, Ischemia, and Lymphoid Abnormalities in Mice Expressing T Cell–Targeted Human Tumor Necrosis Factor Transgenes", J. Immunol., vol. 151, No. 4, pp. 1894–1906, Aug. 15, 1993.

T.J. Schall et al., "Molecular Cloning and Expression of a Receptor for Human Tumor Necrosis Factor", Cell, vol. 61, pp. 361–370, Apr. 20, 1990.

P. Seckinger et al., "Purification and Biologic Characterization of a Specific Tumor Necrosis Factor α Inhibitor", J. Biol. Chem., vol. 264, No. 20, pp. 11966–11973, Jul. 15, 1989.

D. Wallach, "Preparations of Lymphotoxin Induce Resistance to Their Own Cytotoxic Effect", J. Immunol., vol. 132, No. 5, May, 1984.

TIME (Days Post-Implantation)

Fig. 9

TIME (Days Post-Inoculation)

Fig. 10

TIME (Days Post-Implantation)

Fig. 11

TIME (Days Post-Inoculation)

PHARMACEUTICAL COMPOSITIONS FOR CONTROLLED RELEASE OF SOLUBLE RECEPTORS

CROSS REFERENCE TO RELATED APPLICATIONS

The present application is the national stage under 35 U.S.C. §371 of international application PCT/US96/03121, filed Mar. 1, 1996, and claims priority from Israeli application 112,834, filed Mar. 1, 1995.

FIELD OF THE INVENTION

The present invention relates to pharmaceutical compositions for controlled delivery of soluble forms of receptors from a polymeric matrix.

BACKGROUND OF THE INVENTION

Controlled release systems deliver a drug at a predetermined rate for a definite time period, that may range from days to years. These systems provide advantages over conventional drug therapies. For example, after ingestion or injection of standard dosage forms, the blood level of the drug rises, peaks, and then declines. Since each drug has a therapeutic range above which it is toxic and below which it is ineffective, oscillating drug levels may cause alternating periods of ineffectiveness and toxicity. In contrast, a controlled release preparation maintains the drug in the desired therapeutic range by a single administration. Other potential advantages of controlled release system include: (i) localized delivery of the drug to a particular body compartment, thereby lowering the systemic drug level; (ii) preservation of medications that are rapidly destroyed by the body (this is particularly important for biologically sensitive molecules such as proteins); (iii) reduced need for follow up care; (iv) increased comfort; and (v) improved compliance.

Optimal control of drug release may be achieved by placing the drug in a polymeric material. Polymeric materials generally release drugs by diffusion, chemical reaction, or solvent activation.

The most common release mechanism is diffusion, whereby the drug migrates from its initial position in the polymeric system to the polymer's outer surface and then to the body. Diffusion may occur through a reservoir, in which a drug core is surrounded by a polymer film, or in a matrix, where the drug is uniformly distributed through the polymeric system. Drugs can also be released by chemical reaction such as degradation of the polymer or cleavage of the drug from a polymer backbone.

Combinations of the above mechanisms are possible. Release rates from polymeric systems can be controlled by the nature of the polymeric material (for example, crystallinity or pore structure for diffusion controlled systems; the hydrolytic lability of the bonds or the hydrophobicity of the monomers for chemically controlled systems) and the design of the system (for example, thickness and shape). The advantage of having systems with different release mechanisms is that each can accomplish different goals.

For many years, controlled release systems were only capable of slowly releasing drugs of low molecular weight (<600). Large molecules, such as proteins, were not considered feasible candidates, because polypeptides were considered too large to slowly diffuse through most polymeric materials, even after swelling of the polymer. The discovery that matrices of solid hydrophobic polymers containing powdered macromolecules enabled molecules of nearly any size to be released for over 100 days permitted controlled delivery of a variety of proteins, polysaccharides, and polynucleotides. See Langer, 1990.

The proteins and polypeptides incorporated up to this date in polymeric materials for controlled release are mainly effector molecules, such as insulin, as opposed compositions for controlled release of molecules that will bind and neutralize effector molecules produced in the human body.

Tumor necrosis factor-$\alpha$ (TNF$\alpha$) is a potent cytokine which elicits a broad spectrum of biological responses. TNF$\alpha$ is cytotoxic to many tumor cells and may be used in the treatment of cancer. TNF$\alpha$ enhances fibroblast growth and acts as a tissue remodeling agent, being thus suitable in wound healing. It further induces hemorrhagic necrosis of transplanted tumors in mice, enhances phagocytosis and cytotoxicity of polymorphonuclear neutrophils, and modulates the expression of many proteins, including lipoprotein lipase, class I antigens of the major histocompatibility complex, and cytokines such as interleukin-1 and interleukin-6. TNF$\alpha$ has been shown to have an effect against virus, bacteria and multicellular, particularly intracellular, parasites. TNF$\alpha$ appears to be necessary for a normal immune response, but large quantities produce dramatic pathogenic effects. TNF$\alpha$ has been termed "cachectin" since it is the predominant factor responsible for the wasting syndrome (cachexia) associated with neoplastic disease and parasitemia. TNF$\alpha$ is also a major contributor to toxicity in gram-negative sepsis, since antibodies against TNF$\alpha$ can protect infected animals.

TNF$\alpha$ has been shown to be involved in several diseases, examples of which are adult respiratory distress syndrome, pulmonary fibrosis, malaria, infectious hepatitis, tuberculosis, inflammatory bowel disease, septic shock, AIDS, graft-versus host reaction, autoimmune diseases, such as rheumatoid arthritis, multiple sclerosis and juvenile diabetes, and skin delayed type hypersensitivity disorders.

Evidence that some of the effects of TNF$\alpha$ can be detrimental to the host have attracted attention to the mechanisms that regulate TNF$\alpha$ function. The intracellular signals for the response to TNF$\alpha$ are provided by cell surface receptors (herein after TNF-R), of two distinct molecular species, to which TNF$\alpha$ binds at high affinity.

The cell surface TNF-Rs are expressed in almost all cells of the body. The various effects of TNF$\alpha$, the cytotoxic, growth-promoting and others, are all signalled by the TNF receptors upon the binding of TNF$\alpha$ to them. Two forms of these receptors, which differ in molecular size, 55 and 75 kilodaltons, have been described, and will be called herein p55 and p75 TNF-R, respectively. It should be noted, however, that there exist publications which refer to these receptors also as p60 and p80 TNF-R.

Both receptors for TNF$\alpha$ exist not only in cell-bound, but also in soluble forms, consisting of the cleaved extracellular domains of the intact receptors, derived by proteolytic cleavage from the cell surface forms. These soluble TNF$\alpha$ receptors (sTNF-Rs) can maintain the ability to bind TNF$\alpha$ and thus compete for TNF$\alpha$ with the cell surface receptors and thus block TNF$\alpha$ activity. The sTNF-Rs thus function as physiological attenuators of the activity of TNF$\alpha$, safeguarding against its potentially harmful effects. It has, however, also been reported that the sTNF-Rs affect TNF$\alpha$ function also by stabilizing its activity, most likely by preventing dissociation of its bioactive trimeric structure to inactive monomers (Aderka et al., 1992). Thus, the sTNF-Rs may affect TNF$\alpha$ activity in two different ways: either they compete for TNF$\alpha$ with the cell surface receptors and block TNFα deleterious effects, or they act as buffering agents and stabilize TNFα activity.

The two sTNF-Rs, hereinafter p55 sTNF-R and p75 sTNF-R, have been formerly designated TNF Binding Proteins I and II, or TBPI and TBPII, respectively (see, for example, EP 398327, EP 412486, and EP 433900). In the present application we will use both designations: p55 sTNF-R or TBPI and p75 sTNF-R or TBPII; by either designation the proteins are the same.

The sTNF-Rs are present constitutively in serum at concentrations that increase significantly in both inflammatory and non-inflammatory disease states. The effect of these proteins may differ, however, depending on their concentrations at the site of TNFα action, the relation of their concentration to the local concentration of TNFα, and the rates at which the sTNF-Rs and TNFα are cleared from the site of TNFα action in relation to the rate of decay of TNFα activity. Dependent on these parameters, the sTNF-Rs may, in different situations, affect the function of TNFα in quite a different manner, either by inhibiting the effects of TNFα, or serving as carriers for TNFα or even augmenting the effects of TNFα by prolonging its function (Aderka et al., 1992).

The effectivity of the sTNF-Rs as anti-TNFα drugs can be affected by a number of different factors: The affinity at which the sTNF-Rs bind TNFα, compared to the affinity of the cell-surface receptors, the accessibility of the soluble receptors to the site of TNFα action and the rate of the clearance of the soluble receptors and of the complexes which they form with TNFα from the site of TNFα formation. The natural forms of the sTNF-Rs are likely to act in the most physiologically relevant manner. However, a major limitation in their use is their rather rapid clearance from the blood. Several attempts have been made to improve these molecules, examples of which are the so-called chimeric "immunoadhesins", in which the sTNF-Rs are linked to the Fc portion of the immunoglobulin molecule (developed by Hoffman La Roche and Immunex), and "PEGulated" sTNF-Rs, in which the sTNF-Rs are cross-linked through PEG molecules (developed by Synergen). Both approaches result in formation of divalent sTNF-R molecules which have longer clearance time and can bind more effectively to the trivalent TNFα molecule. However, they are quite likely to be more immunogenic than the natural soluble receptors, and the clearance of their complex with TNFα from the circulation may not occur at a sufficient efficiency.

Many harmful effects of TNFα result from chronic formation of this cytokine at certain distinct loci in the body. A major foreseen limitation to the use of soluble forms of TNF receptors for defense against such pathological conditions is the difficulty in maintaining therapeutically effective concentration of the soluble receptors, for prolonged durations, at sites of need.

SUMMARY OF THE INVENTION

It is an object of the present invention to develop novel approaches for therapeutic applications of soluble forms of receptors for affecting the functions of their ligands, e.g., for protection against deleterious effects of their ligands, particularly systems which allow local release of the soluble receptor in the body, at a constant rate and for long duration. These approaches are based on incorporation of the soluble receptor into biocompatible polymeric materials, which are implanted or injected in desired bodily compartments. Matrices of polymers containing the soluble receptor enable local and controlled release of the soluble receptor, in its natural form.

Any soluble receptor that is capable of binding to and affecting the functions of its ligand, either neutralizing the deleterious effects of its ligand and/or stabilizing or augmenting its activity, is encompassed by the invention. Examples of such soluble receptors are the soluble receptors of hormones and of cytokines, and in a preferred embodiment, the soluble receptor is a soluble TNFα receptor.

Thus, another object of the present invention is to provide a novel approach for therapeutic applications of soluble TNFα receptors for affecting TNFα effects, e.g., for protection against TNF effects, involving controlled release systems.

The present invention thus provides a pharmaceutical composition for controlled release of a soluble receptor, wherein said soluble receptor is incorporated into a biocompatible polymer matrix.

Examples of biocompatible polymeric materials that can be used in the compositions of the invention include, but are not limited to, biocompatible nondegradable polymers selected from the group comprising ethylene-vinyl acetate copolymers (EVAc), silicone rubbers, polysaccharides such as cellulose, polyamides, polyacrylates, polyethylenes, polyurethanes, polyisobutylene, and polyphosphazenes, and biodegradable polymers selected from the group comprising polyesters, polyanhydrides, polyorthoesters, polycaprblactone, pseudopolyaminoacids, polypeptides, gelatin, polylactic acid, polyglycolic acid and poly lactic-glycolic acid (PLGA) copolymers.

In one preferred embodiment, a soluble TNFα receptor (sTNF-R) is incorporated in a suitable polymeric material, such as a polyethylene-vinyl acetate matrix, or into poly (lactic-glycolic acid) microspheres.

Pharmaceutical compositions according to the present invention may contain the p55 sTNF-R or p75 STNF-R. In a preferred embodiment, the composition contains the p55 sTNF-R (TBPI).

In one embodiment, the pharmaceutical compositions of the invention are for use in the treatment of disorders in which protection against the deleterious effects of the ligand, e.g., TNFα, is desired. The polymeric matrices containing the sTNF-Rs are placed in desired bodily compartments, thus allowing maintenance of the sTNF-R in the body constantly and for long duration.

In another embodiment, the pharmaceutical compositions of the invention are for use together with the ligand, e.g., TNFα, in order to stabilize and or augment TNFα activity, for use in any situation in which a beneficial effect of TNFα is desired. In one aspect of this embodiment, the composition comprises a TNFα/sTNF-R complex, which, by administration at tumor sites, may allow effective local antitumor function and little systemic undesired effects of TNFα. In other aspects of this embodiment, the composition comprising the TNFα/sTNF-R complex is useful against viral, bacterial and parasiticidal, particularly intracellular multicellular parasiticidal, infections, and for wound healing.

In another embodiment, the invention comprises treatment of a patient to protect said patient from the deleterious effects of a ligand, e.g., TNFα, which comprises administering to said patient a pharmaceutical composition according to the invention comprising an effective amount of the suitable soluble receptor, e.g., sTNF-R, in controlled release form.

In a further embodiment, the invention relates to treatment of cancer, which comprises administering at the tumor site of a patient in need thereof a pharmaceutical composition of the invention comprising a TNFα/sTNF-R complex in controlled release form.

BRIEF DESCRIPTION OF THE DRAWINGS

FIGS. 4a–c show in vivo results of Balb nude mice inoculated with TNF-producing Chinese hamster ovary (CHO) cells (CHO/TNF) and treated with TBPI or with mouse anti-TNF monoclonal antibody TNF-1(Ab), wherein:

FIG. 4b presents the results of an in vitro assessment of bioactive TNFα levels in mice sera. The sera was collected from mice bearing TNFα-producing Chinese hamster ovary (CHO) cells, at the indicated time periods after implantation of TBPI in EVAc (closed circles) or of TBPI in PLGA 75:25 (open circles), or injection of anti-TNFα antibody injected once (closed squares) or twice (open squares) as in FIG. 4a, as well as from non treated mice (closed triangles), TNFα bioactivity in the sera was determined by applying them at a dilution of 1:100 to cultured MHA2 cell (a derivative of HeLa cells, 24 hours after seeding them at $3 \times 10^4$ cells per 9 mM microwell) for 10 hours, in the presence of cyclo-heximide (25 μg/ml), followed by assessment of cell viability by the neutral red uptake method (Wallach et al., 1984)

DETAILED DESCRIPTION OF PREFERRED EMBODIMENTS

The present invention provides for controlled release of any soluble receptor which can bind to and affect the activity of its ligand, such as neutralizing a ligand that has deleterious effects or stabilizing/augmenting a ligand's activity. Examples of such soluble receptors are the soluble receptors of cytokines, e.g., TNFα, IFN-γ, IL-2, IL-6 and the like.

In a preferred embodiment, the compositions of the invention comprise sTNF-Rs that may be obtained from natural sources, such as human urine (Engelmann et al., 1989; Engelmann et al., 1990; Olson et al., 1989, and Seckinger et al., 1989) or by recombinant techniques (EP 433900; Nophar et al., 1990; Schall et al., 1990, and Loetscher et al., 1990), and then further purified as described, for example, in EP 308378 and EP 398327.

As used herein, the terms "sTNF-Rs", "p55 sTNF-R", "p75 sTNF-R", refer to all sTNFs from natural sources or obtained by recombinant DNA techniques, including but not limited to the TNF Binding Proteins I and II described in EP 308378 and EP 398327.

Polymers that can be used in the present invention include, but are not limited to, biocompatible nondegradable polymers selected from ethylene-vinyl acetate copolymers, silicone rubbers, polysaccharides such as cellulose, polyamides, polyacrylates, polyethylenes, polyisobutylene, polyurethanes and polyphosphazenes, and biodegradable polymers selected from polyesters, polyorthoesters, polycaprolactone, polypeptides, pseudo poly(amino acids), gelatin, polyanhydrides, poly-L-lactic acid, poly-D-lactic acid, poly-D,L-lactic acid, polyglycolic acid, and copolymers selected from poly-L-lactic acid-glycolic acid, poly-D-lactic acid-glycolic acid, poly-D,L-lactic acid-glycolic acid, poly-L-lactic acid-D-lactic acid, and poly-L-lactic acid-D, L-lactic acid.

The polymers preferably used in the present invention are ethylene-vinyl acetate copolymers (EVAc), poly lactic-glycolic acid copolymers (PLGA) and poly-L-lactic acid (PLLA).

A pharmaceutical composition comprising sTNF-R incorporated in an EVAc matrix may be prepared from commercially available EVAc, after purification, if necessary, for example, by solvent casting as described by Rhine et al., 1980. These matrices constitute diffusion-controlled systems that allow uniform protein distribution, reproducible kinetics and prolonged release of biologically active sTNF-R over a period of weeks or even months. As EVAc is a biocompatible but nondegradable polymer, EVAc matrices are suitable for use in applications in which extended drug delivery is required or desired.

As the active principle is released from nondegradable polymeric materials such as EVAc by means of diffusion through channels in the matrix, diffusion is enhanced by higher protein loading. Thus, in a preferred embodiment, the active protein is combined with a neutral protein which does not affect the biological response to the active protein in order to increase the total protein load. Examples of such neutral proteins are bovine serum albumin (although this is not preferred for human use), human albumin, myoglobin, hemoglobin, etc.

In a pharmaceutical composition according to the invention comprising sTNF-R incorporated into a biodegradable polymer selected from the group comprising poly-L-lactic acid, polyglycolic acid, and copolymers thereof, commercially available homopolymers or copolymers of lactic acid and/or glycolic acid are compounded in the form of microspheres, suitable both for application as implants or as injections. The microspheres can be prepared, for example, by the modified solvent evaporation method using a double emulsion as described by Cohen et al., 1991. As these polymers are biodegradable, the implant can be easily injected, avoiding the use of surgical procedures and the need to remove the device after the drug is depleted. The active agent is released by controllable and predictable release kinetics. The system allows prolonged release of the active agent over a period of weeks or even months.

The pharmaceutical composition of the invention comprising a sTNF-R may be used to neutralize the deleterious effects of TNFα in acute diseases, such as septic shock, graft-versus-host disease (GVHD), malaria, infectious hepatitis, tuberculosis, or in chronic diseases, such as cancer-associated cachexia, chronic GVHD, or in autoimmune diseases, e.g., rheumatoid arthritis, juvenile diabetes, systemic lupus erythematosus and multiple sclerosis, or in skin delayed-type hypersensitivity disorders.

The pharmaceutical composition of the invention may be administered by any mode suitable for controlled delivery of the sTNF-R, either as implants, or as local injections, for example, intra-articular injection given into the synovial fluid of the joint cavities in the treatment of rheumatoid arthritis, or intrathecal injection given into the cerebrospinal fluid in the treatment of multiple sclerosis, or topical formulations, e.g., lotions, for treatment of skin disorders. The compositions for treatment of rheumatoid arthritis may comprise other anti-inflammatory agents, and the compositions for treatment of multiple sclerosis may comprise other agents against multiple sclerosis, e.g., beta-interferon and Copolymer-1 (Cop-I).

The composition of the invention comprising STNF-R will be so designed as to deliver in the body an amount of sTNF-R sufficient for blocking TNFα action. In the case of autoimmune diseases, the composition will be designed such as to deliver an amount of sTNF-R that is sufficient to affect the course and severity of the autoimmune disease and to improve the patient's condition, leading to reduction or remission of the disease. The effective amount will depend on the route of administration, the disease to be treated and the condition of the patient. Determination of the level of p55 sTNF-R or p75 sTNF-R in the serum or other suitable body fluid of the patient by known methods (for ELISA, see Aderka et al., 1991), may help to establish a suitable dose for said patient, considering that the exogenously administered sTNF-R may complement the endogenously formed sTNF-R in neutralizing the TNFα deleterious activity.

When stabilization of TNFα activity is desired, the composition will comprise a complex of TNFα and sTNF-R, for example, a 1:1 complex, for administration at the tumor site.

The invention will now be illustrated in a non-limitative manner by the following examples and the accompanying drawings.

EXAMPLES

Materials and Methods

Materials. PLGA, 50:50, inherent viscosity (i.v.) of 0.51 dl/g, and 75:25, i.v. of 0.48 dl/g, and PLLA (poly-L-lactic acid), i.v. of 0.64 dl/g (both from PURAC Biochem BV, Holland), were used. Ethylene-vinyl acetate copolymer (EVAc), (40% vinyl acetate) (Dupont), bovine serum albumin (BSA) (Sigma Chemical Co., USA), polyvinylalcohol (PVA) of average molecular weight 77000–79000, 88% hydrolyzed (Aldrich Chemical Co.) and TBPI (p55 sTNF-R) (InterPharm Laboratories Ltd., Israel), were used as received. The anti-TNFα antibody designated TNF-1 is a mouse monoclonal antibody raised against human recombinant TNFα in one of the present inventors' laboratory (D. Wallach).

Methods. In vitro release profiles were obtained by placing the drug delivery matrices into phosphate-buffered saline (PBS, pH 7.4) contained in a vial and agitated in a shaker bath. Samples were taken periodically and analyzed for TBPI by Enzyme Linked Immuno Sorbent Assay (ELISA) for TBPI, as described by Aderka et al., 1991.

In vivo efficacy of the polymeric systems was examined on three models: (i) Mice implanted with TNFα-producing tumor cells (CHO/TNF) as described by Oliff et al., 1987, exhibiting severe cachexia leading to death. (ii) Transgenic Tg197 mice which predictably develop arthritis, as described by Keffer et al., 1991. (iii) Transgenic Tg211 mice that express human TNFα mRNA in T cells and develop marked histologic changes and a lethal wasting syndrome, as described by Probert et al., 1993.

Example 1

Controlled release of p55 sTNF-R/TBPI from EVAc matrices

Ethylene-vinyl acetate copolymer (40% vinyl acetate by weight) was dissolved in methylene chloride to give a 10% solution (w/v). TBPI solution was added to bovine serum albumin (BSA) powder dissolved in double distilled water. The mixture was freeze dried (24 hr, at 5 microns Hg and −70° C., Freeze Dryer, Lab Conco) into a powder. TBPI +BSA powder was sieved to give particles of <75, 75–250, or 250–425 pm. A weighed amount of powder from a single size range was added to 15 ml of the polymer solution in a glass vial, and the mixture was poured quickly into the center of a leveled Teflon mold of disks (1 cm in diameter and 0.5 cm in thickness), which had been cooled previously on dry ice for 5 min. During precooling, the mold was covered with a glass plate to prevent excess frost formation. After the mixture was poured, the mold remained on the dry ice for 10 min, and the mixture froze. (The mold was covered again for the last 7 min of this stage.) The frozen slab was easily pried loose with a cold spatula, transferred onto a wire screen, and kept at −20° C. for 2 days. The disk then was dried for 2 more days at room temperature in a desiccator under a mild houseline vacuum (600 mtorr). Drying caused the disks to shrink to ≈0.5 cm in diameter and 0.1–0.2 cm in thickness.

The polymeric delivery systems were immersed in PBS medium. EVAc matrices were prepared as disks of 0.5 cm in diameter and thickness of 1–2 mm containing 22.35 μg of TBPI in every disk for in vivo experiments. For in vitro experiments, the disks contained 4.47, 13.41 or 22.35 μg TBPI (10%, 30% and 50% loading). The release of the TBPI was detected by ELISA for TBPI as a function of time (Aderka et al., 1991).

Figure 1:
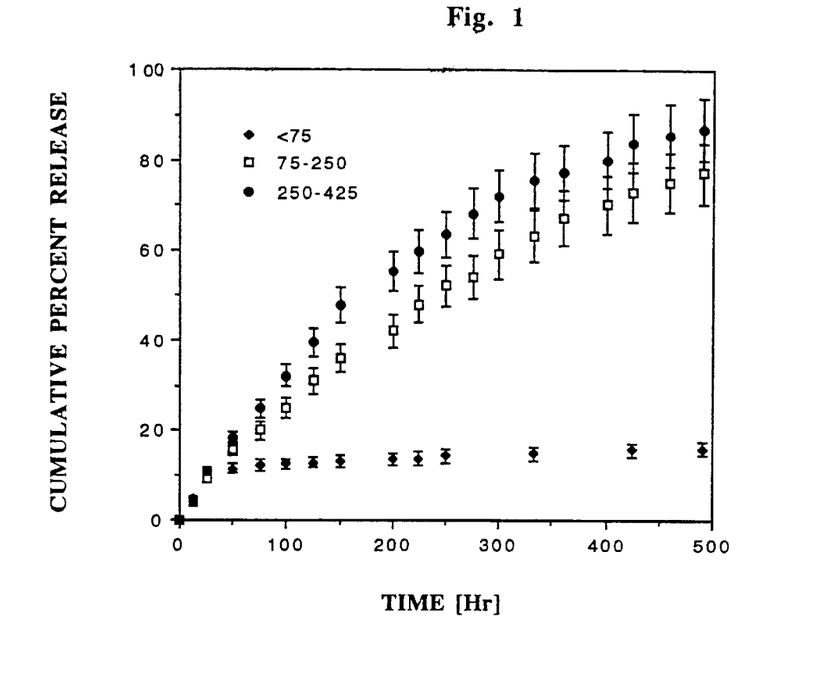
FIG. 1 shows particle size effect on cumulative TBPI release. Particles of TBPI +BSA powder at three size ranges were incorporated into ethylene-vinyl acetate copolymer (EVAc) matrices at 30% loading: (i) <75. pm (closed losanges); (ii) 75–250 μm (open squares), and (iii) 250–425 μpm (closed circles)
Figure 2:
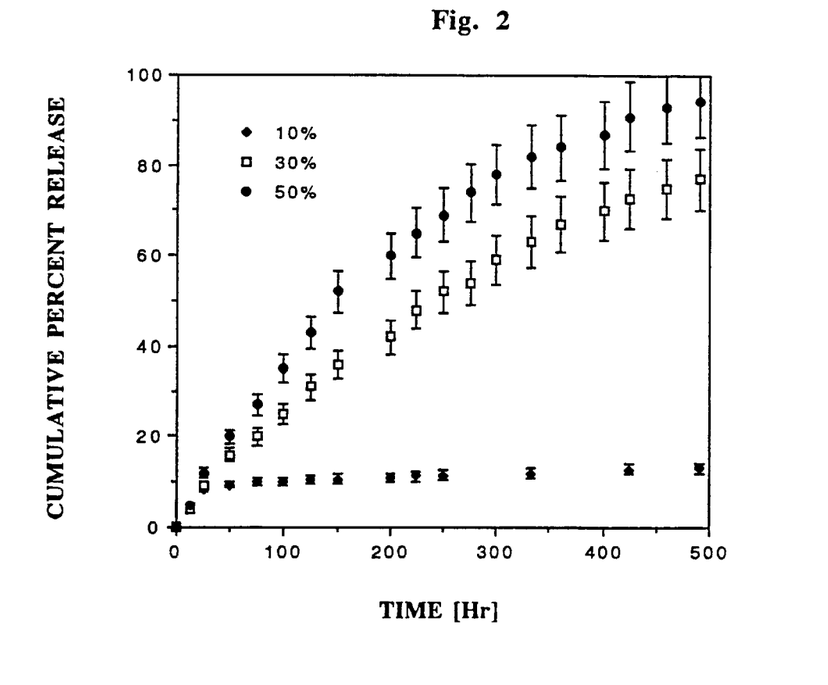
FIG. 2 shows loading effect on cumulative TBPI release. EVAC matrices with loadings of TBPI+BSA were made using particle size range of 75–250 μm: (i) 10% loading (closed losanges); (ii) 306 loading (open squares), and (iii) 50% loading (closed circles).

FIGS. 1 and 2 show the effect of drug particle size and loading on release kinetics from EVAc matrices. Particle size significantly affected the drug release rates. An increase in particle size increased the release rates (FIG. 1). Increase in drug loading uniformly increased drug release rates (FIG. 2). Not only did total drug released increase, but also release rates increased.

Drug particle size and loading markedly affected release kinetics of the macromolecular polymeric delivery systems. Because macromolecules are too large to diffuse through the polymer film, it is possible that sustained release occurs via diffusion through channels in the matrix. The incorporation of the macromolecules during the casting may introduce such channels through which the dissolved drug can diffuse. Release rate increases caused by increases in particle size may result from the formation of larger channels -of pores in the polymer matrix. Similarly, increased loadings may provide simpler pathways (lower tortuosity) and greater porosity for diffusion, both of which would facilitate the movement of water or PBS into, and protein out of, the matrix.

Example 2
Controlled release of p55 STNF-R (TBPI) from PLGA and PLLA microsrheres Poly (lactic-glycolic acid) (PLGA) or poly-L-lactic acid (PLLA) microspheres, were prepared by a modified solvent evaporation method using a double emulsion as described by Cohen et al., 1991. Briefly, TBPI solution or powder of TBPI and BSA (prepared as described in Example 1 above), which was dissolved in double distilled water, were poured into PLGA or PLLA dissolved in methylene chloride. The mixture was probe sonicated (model VC-250, Sonic & Materials Inc.) for 30 sec to form the first inner emulsion (W1/0). The emulsion was poured, under vigorous mixing using magnetic bar, into 2 ml aqueous it polyvinylalcohol (PVA) saturated with methylene chloride to form the second emulsion ((W1/0)W2). The resulting double emulsion was poured into 200 ml of 0.1% PVA and continuously stirred for 3 hr at room temperature until most of the methylene chloride evaporated, leaving solid microspheres. The microspheres were collected by centrifugation (1000 g for 10 min), sized using sieves with apertures of 100 μm and freeze dried (16 hr, Freeze Dryer, Lab Conco) into a powder. Unless specified, studies were done with PLGA with a ratio of 75:25 and 50:50 (L/G) and PLLA.

The polymeric delivery systems were immersed in PBS. 0.04 g of PLGA or PLLA microspheres containing 18.2 μg of TBPI were evaluated in each experiment, and the release of TBPI was detected by ELISA as a function of time.

Figure 3:
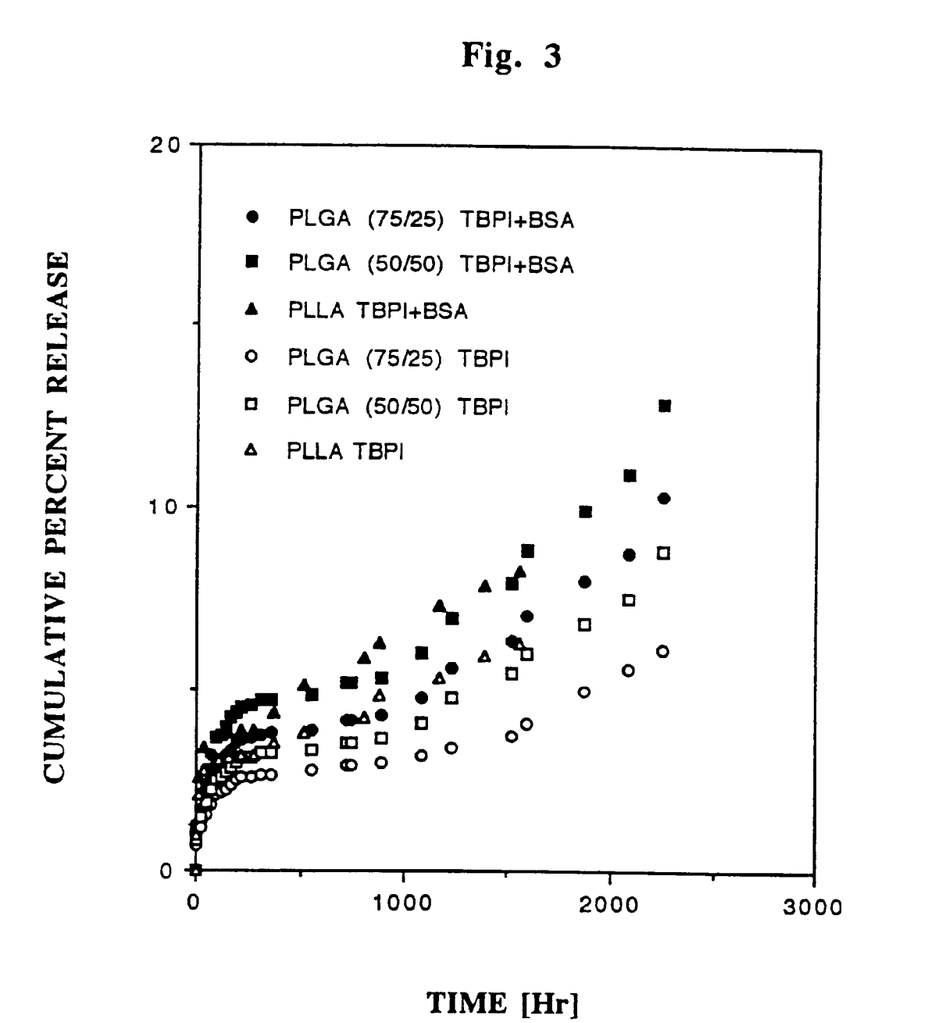
FIG. 3 shows cumulative percent release of soluble TNFα receptor I (TBPI) alone or incorporated together with bovine serum albumin (BSA) from microspheres of: (i) poly lactic-glycolic acid (PLGA) 75:25 (open and closed circles, respectively); (ii) PLGA 50:50 (open and closed squares, respectively; and (iii) poly-L-lactic acid (PLLA) (open and closed triangles, respectively).

FIG. 3 shows the cumulative percent release of TBPI from different PLGA copolymers (50:50 or 75:25) or PLLA microspheres. It can be seen that even after 2200 hours, only 10 percent of the TBPI which was incorporated into the microspheres had been released. It is also shown in this graph that the cumulative percent release of TBPI from polymers where TBPI was added together with BSA (TBP+BSA) (closed circles, squares and triangles) is higher than from samples where TBPI was added without BSA (open circles, squares and triangles).

Example 3
TBPI released from polymer matrices retains its biological activity in vivo in mice inoculated with CRO/TNFα cells As a way of following chronic deleterious effects of TNFα, a well-known animal model for the cachectic effect of TNFα was used in the experiment, i.e., balb-nude mice implanted with TNFα-producing tumor (CHO/TNFα) cells, as described by Oliff et al., 1987.

Balb-nude mice were inoculated subcutaneously with CHO/TNFα cells (Korn et al., 1988) to achieve cachexia. Inoculations were carried out using freshly trypsinized suspensions of cell lines at a concentration of $1 \times 10^7$ cells/ml (1 ml/mouse). Injections were performed via 23-gauge needles on plastic 3 cc syringes. The cells were injected subcutaneously in the back, neck or abdomen region. Serum samples were obtained several times every week by tail bleeding. The performance of the polymeric systems, implanted five days after mice inoculation with CHO/TNFα cells, was evaluated following the levels of TBPI and TNFα in blood, weight decrease and mortality.

Polymeric matrices according to Examples 1 and 2 above were implanted or injected in the balb-nude mice five days after mice inoculation subcutaneously with TNFα-producing CHO cells to achieve cachexia and their performance was evaluated following the levels of TBPI and TNFα in blood (ELISA). The parameters examined were: (1) biological activity of TBPI as function of time; (2) comparison of TBPI treatments to treatment with mouse antibodies against human TNFα (raised in the inventors' laboratories and designated TNF-1) injected once (five days after mice inoculation with CHO/TNFα cells, marked as Ab-once) or twice by interval of one i week from each other (five days after mice inoculation with CHO/TNFα cells and a one week later, marked as Ab-twice); (3) the progress of cachexia in terms of mice average group weight and mice mortality; and (4) site of implantation (subcutaneous in the neck, back or stomach).

TNFα may cause cachexia, and can induce progressive weight loss in tumor-bearing animals. The in vivo efficacy of the matrices was examined in mice implanted with TNFα-producing tumor cells. Mice injected with $1 \times 10^7$ CHO/TNFα cells that produce constitutively TNFα at high levels, exhibited severe cachexia and weight loss, leading to death. Mice that, in addition, were implanted with matrices of polymers containing TBPI, increased their body weight without mortality, indicating that the TBPI released from the matrices provided long-lasting protection against TNFα.

Figure 4A:
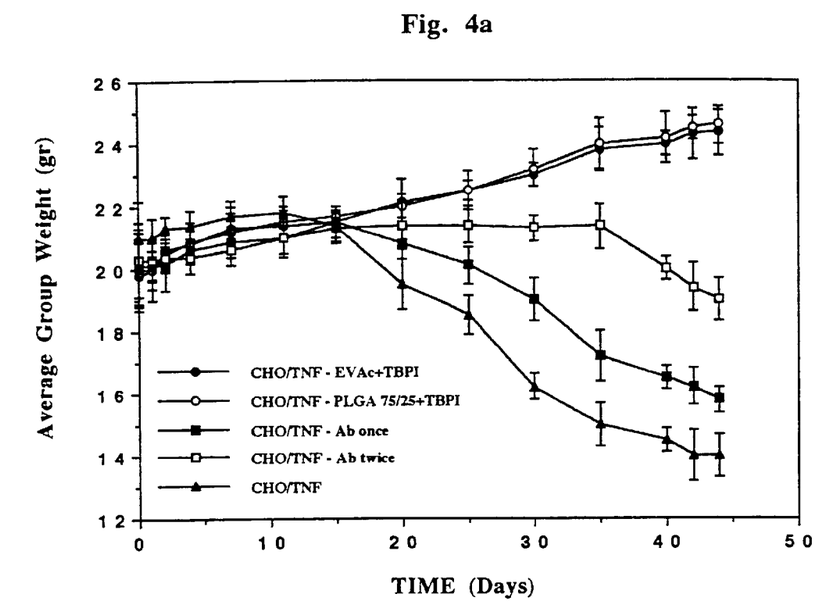
FIG. 4a is a graphic representation of average group weight (gr) of Balb nude mice treated with: (i) TBPI in EVAc matrix implanted subcutaneously (closed circles); (ii) TBPI in PLGA 75:25 implant (open circles); (iii) anti-TNF antibody injected once, five days after mice inoculation with CHO/TNF cells (Ab once) (closed squares); (iv) anti TNF antibody injected twice, five days after mice inoculation with CHO/TNF cells and a one week later (Ab twice) (open squares); and (v) control, without any treatment (closed triangles)
Figure 4B:
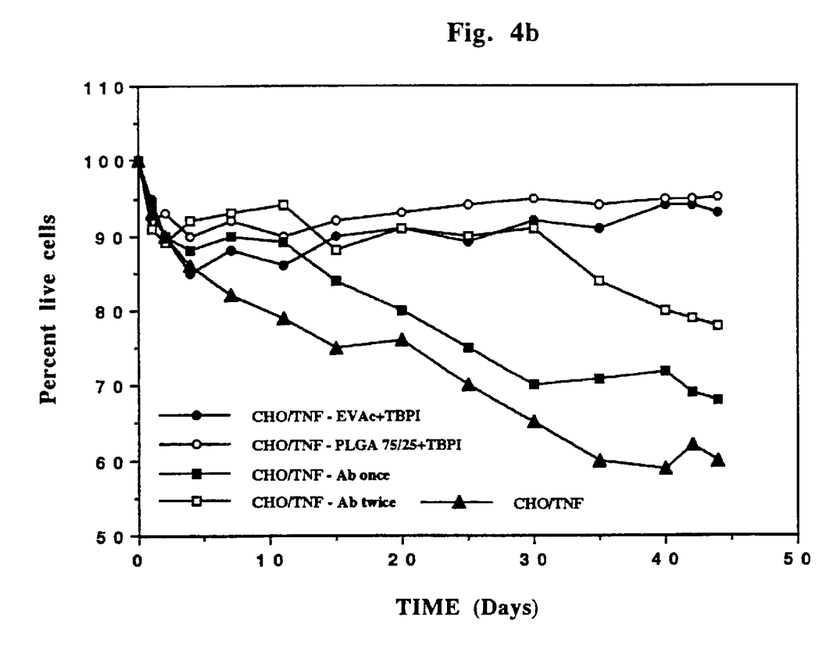
FIG. 4c represents survival curves for mice treated with: (i) TBPI in EVAC implant (open squares); (ii) TBPI in PLGA 75:25 implant (closed circles); (iii) anti-TNF antibody once (open triangles); (iv) anti-TNF antibody twice (closed triangles); and (v) control, without any treatment (open circles).

To assess the biological activity of TBPI in the tumor-bearing mice, serum samples were collected at various time points and the bioactivity of TNFα in them was estimated by determining their cytotoxicity to MHA2 cells (a derivative of HeLa cells that are sensitive to TNFα). As shown in FIG. 4b, inoculation of the TBPI-containing matrices resulted in prolonged and significant reduction in serum TNFα bioactivity, indicating that the TBPI released from the matrices inhibits strongly the binding of TNFα to the cell surface TNFα receptors on the MHA2 cells.

For comparison, mice were injected with antibodies to TNFα once (five days after mice inoculation with CHO/TNFα cells, marked as Ab-once) or twice (five days after mice inoculation with CHO/TNFα cells and a one week later, marked as Ab-twice). As shown in FIG. 4a, antibodies affected mice weight only for few days from time of injection (mice maintained their body weight), and then they developed progressive wasting, while TBPI, when incorporated into polymers, was present in the body for long time.

The short duration of the effect of injected anti-TNFα antibodies (TNF-1) is manifested also in the pattern is of TNFα bioactivity in the sera of the antibody-injected mice, as shown in FIG. 4b.

Figure 4C:
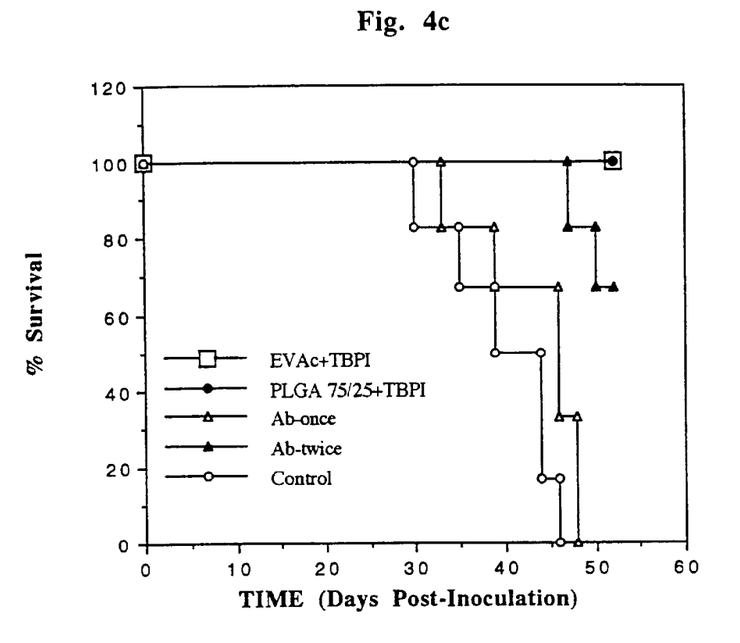

In FIG. 4c it can be seen that mice treated with polymeric systems which permit the controlled and localized release of TBPI, survived for more than 50 days, in contrast to mice treated with the TNF-1 antibodies, that did not survive and developed cachexia when the injections of antibodies were stopped.

These results indicate that treatment based on polymeric controlled delivery of TBPI prevents development of the wasting syndrome, and might be preferred to injection of antibodies to TNFα, since it eliminates the need to inject every week and provides longer-lasting protection against TNFα. Moreover, being natural molecules, the soluble TNFα receptors are more suitable for prolonged use. Anti-TNFα antibodies will sooner or later raise antibodies against them, which will prevent their action, and are therefore not suitable for prolonged use. This is true also for human or humanized antibodies, that will raise anti-idiotypic antibodies that will block their function.

Figure 5:
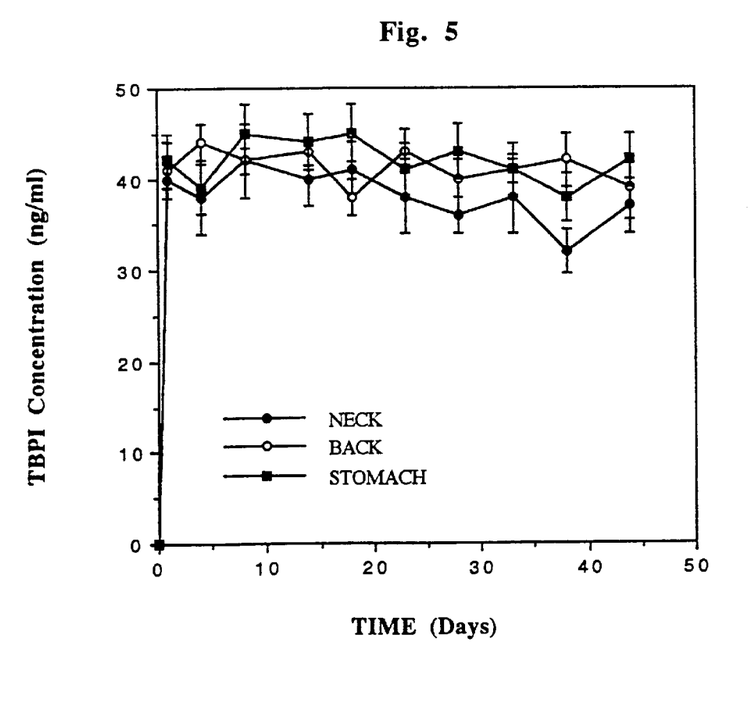
FIG. 5 shows effect of implantation of EVAc matrices containing TBPI in different sites of the mouse body on TBPI concentration release: neck (closed circles), back (open circles), and stomach (closed squares).

There is no significant difference in TBPI release kinetics from matrices of EVAc implanted in the mice neck, back or stomach, as function of implantation site of the matrices (FIG. 5). The TBPI release kinetics is constant along all the release duration.

Example 4

Figure 6:
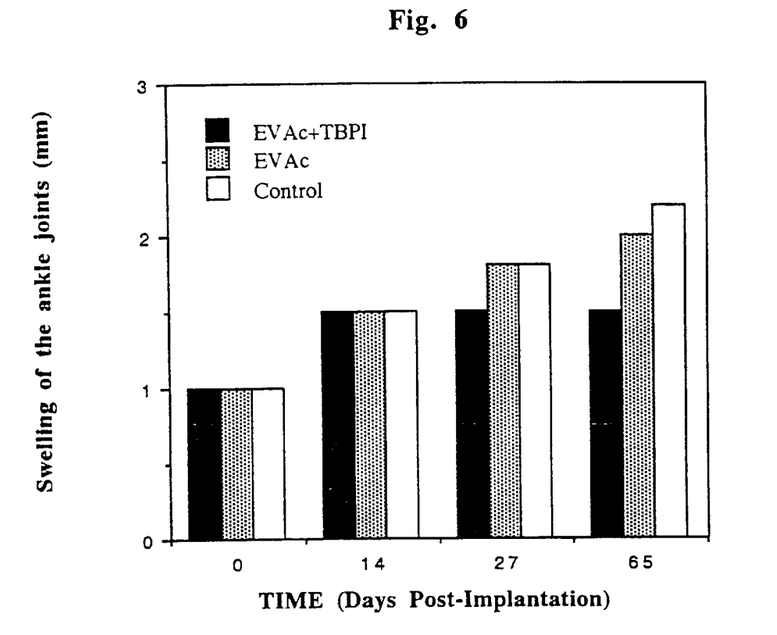
FIG. 6 is a graphic representation of the swelling of the ankle joints (mm) showing progression of arthritis at different development stages of transgenic Tg 197 arthritic mice progeny treated with implants of EVAc comprising TBPI (black columns), EVAc alone (grey columns) or untreated (control) (white columns).

TBPI release from polymer matrices retains its biological activity in vivo in transgenic arthritic Tg197 mice The performance of EVAC matrices made in accordance with Example 1 (implanted subcutaneously by minor surgery 14 days from birth) in transgenic Tg197 mice was evaluated following the levels of swelling of the ankle joints. The disease was evident at around 4–6 weeks of age with swelling of the ankle joints. Additional swelling of the ankle joints and impairment in leg movement progressed to complete loss of movement of the hind legs at around 9–10 weeks of age. Moreover, progressive weight loss was a common feature in these mice. Treatment of these arthritic mice with EVAc matrices containing TBPI, however, completely prevented swelling of the ankle joints (FIG. 6). Moreover, treated animals developed normally and showed no signs of arthritis or weight loss even past 10 weeks of age.

Figure 7:
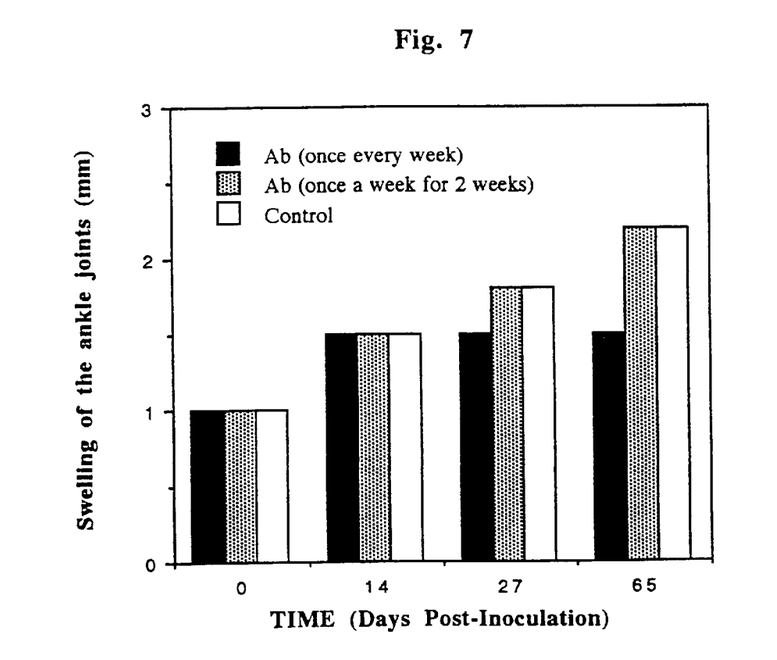
FIG. 7 is a graphic representation of the swelling of the ankle joints (mm) showing progression of arthritis at different development stages of transgenic Tg 197 arthritic mice progeny treated with anti-TNFα antibodies once every week for the experiment duration (65 days) (black columns) and once a week for two weeks (grey columns) or untreated (control) (white columns).

For comparison, mice were injected 14 days from birth with TNF-1 antibodies once every week for all treatment duration (65 days), or once a week for 2 weeks. As shown in FIG. 7, the antibodies affected swelling only if given once every week for all the experiment duration (black columns). Mice that were injected every week developed normally and showed no signs of arthritis or weight loss even past 10 weeks of age, when impairment of movement is a common macroscopial feature in these mice. However, mice that were injected once a week for 2 weeks developed swelling of the ankle joints and impairment in leg movement progressed to complete loss of movement of the hind legs at around 9–10 weeks of age with progressive weight loss.

These results indicate that treatment based on polymeric controlled delivery of TBPI completely prevents development of arthritis in mice, and might be preferred to injection of antibodies to hTNFα, since it provides longer-lasting protection against TNFα and eliminates the need of injection every week.

Example 5

TBPI released from polymeric matrices retains its biological activity in vivo in transgenic Tg211 mice Transgenic Tg211 mice that express human TNF mRNA in T cells developed marked histologic changes and a lethal wasting syndrome. The performance of the polymeric systems containing TBPI, implanted 14 days from birth, was evaluated following the weight decrease and mortality. The individual animals were weighed several times every week. EVAc matrices were implanted subcutaneously by minor surgery.

Figure 8:
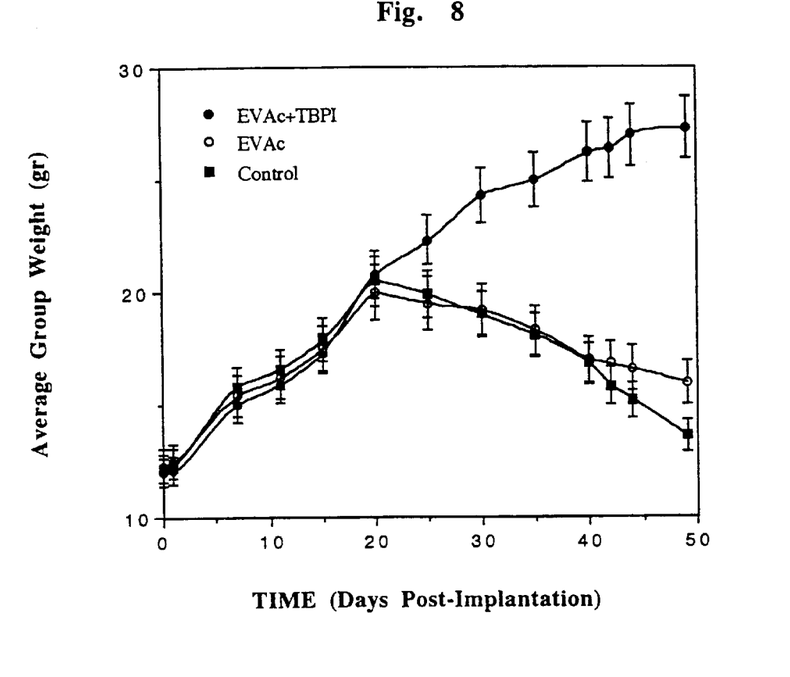
FIG. 8 is a graphic representation of the average group weight (gr) of transgenic Tg 211 mice that express human TNFα mRNA in T cells, treated with implants of EVAc comprising TBPI (closed circles), EVAc alone (open circles) or untreated (control) (closed squares).
Figure 10:
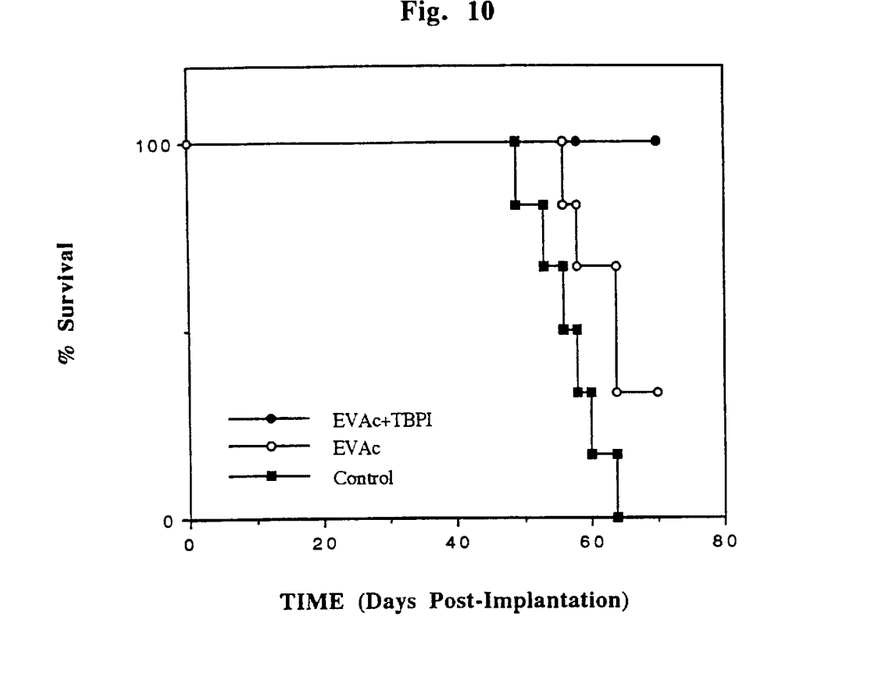
FIG. 10 represents survival curves for transgenic Tg 211 mice treated with implants of EVAc comprising TBPI (closed circles) and EVAC alone (open circles) or untreated (control) (closed squares).

As shown in FIGS. 8 and 10, untreated mice (control group: closed squares) developed severe progressive weight loss, leading to death, while mice that were implanted with EVAc matrices containing TBPI (closed circles), increased their body weight and survived for all experiment duration.

Figure 9:
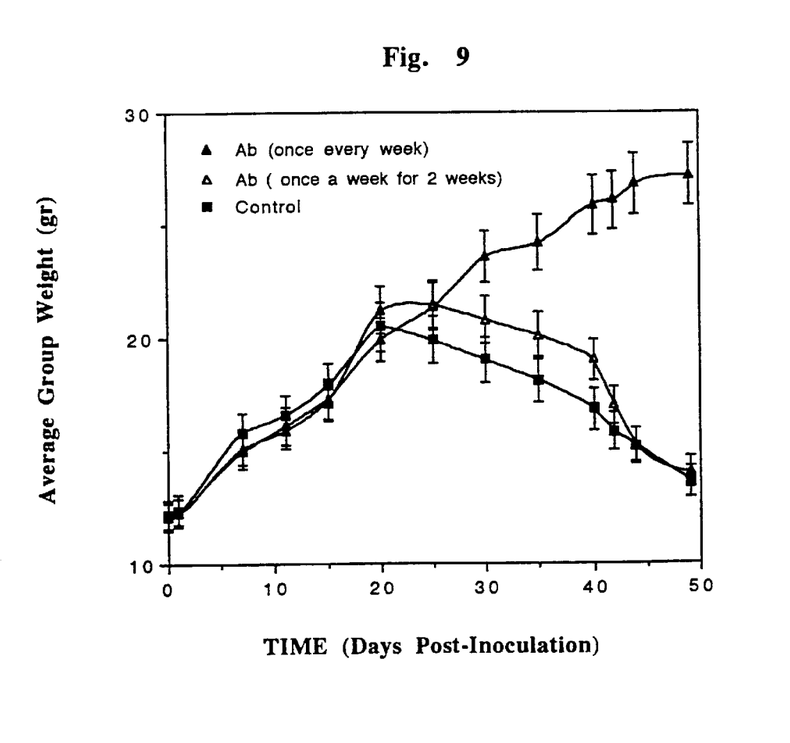
FIG. 9 is a graphic representation of the average group weight (gr) of transgenic Tg 211 mice treated with anti-TNFα antibodies once every week for experiment duration (50 days) (closed triangles), and once a week for 2 weeks (open triangles) or untreated (control) (closed squares).
Figure 11:
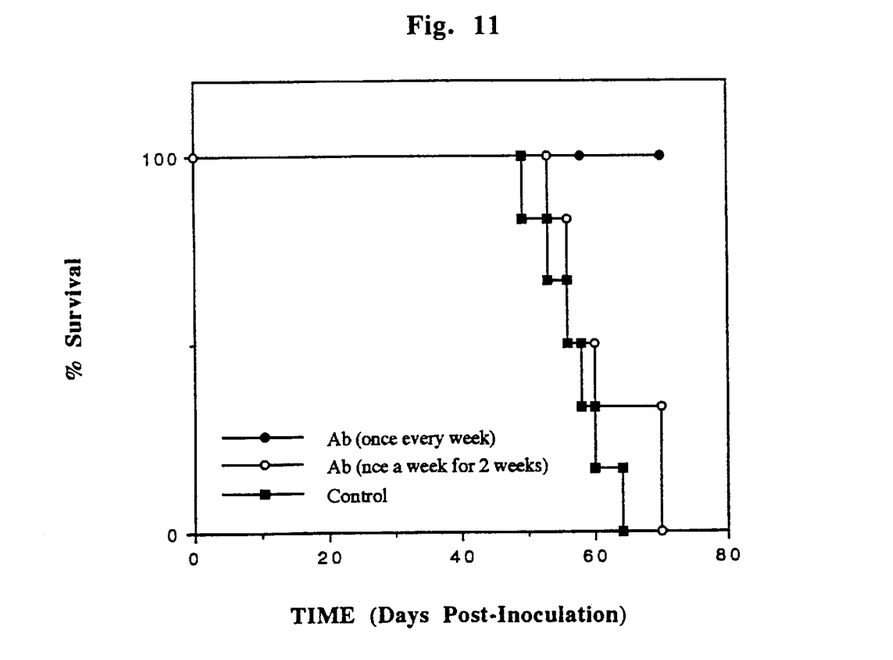
FIG. 11 represents survival curves for transgenic Tg 211 mice treated with anti-TNFα antibodies once every week for 65 days (closed circles), and once a week for 2 weeks (open circles) or untreated (control) (closed squares).

For comparison, mice were injected 14 days from birth with TNF-1 antibodies once every week for all experiment duration, or once a week for 2 weeks. As shown in FIG. 9, administration of anti-TNFα antibodies completely prevented development of the wasting syndrome if given from birth every week. However, if given only once a week for 2 weeks, they were not effective, and mice developed the wasting syndrome which lead to death, as shown in FIG. 11.

These results indicate that treatment based on polymeric controlled delivery of TBPI completely prevents development of the wasting syndrome in mice, and might be preferred to injection of antibodies to hTNFα.

The in viva results indicate that TBPI released retains its biological activity, as shown by the average group weight change (FIG. 4a) and the high percent of live MHA2 cells that are sensitive to TNFα (FIG. 4b).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Aderka D. et al., *Cancer Res.*, 51:5602–5607 (1991).
2. Aderka D. et al., *J. Exp. Med.*, 175:323–329 (1992).
3. Cohen S. et al., *Pharm. Res.*, 8:713–720 (1991).

4. Engelmann H. et al., *J. Biol. Chem.,* 264:11974–80 (1989).
5. Engelmann H. et al., *J. Biol. Chem.,* 265:1531–36 (1990).
6. Korn J. H. et al., *Lymphokine Res.,* 7:349–358 (1988).
7. Langer R., *Science,* 249:1527–1533 (1990).
8. Loetscher H. et al., *Cell,* 61:351–359 (1990).
9. Nophar Y. et al., *EMBO J.,* 9:3269–78 (1990).
10. Oliff A. et al., *Cell,* 50:555–563 (1987).
11. Olson I. et al., *Eur. J. Haematol.,* 42:270–75 (1989).
12. Probert L. et al., *J. Immunol.,* 151:1894–1906 (1993).
13. Rhine W. D. et al., *J. Pharm. Sci.,* 69:265–270 (1980).
14. Schall T. J. et al., *Cell,* 61:361–370 (1990).
15. Seckinger P. et al., *J. Biol. Chem.,* 264:11966–973 (1989).
16. Wallach D. et al., *J. Immunol.,* 132:2464–69 (1984).

What is claimed is:

1. A pharmaceutical composition for the treatment of disorders in which amelioration of the deleterious effects of Tumor Necrosis Factor-α is required, comprising a biocomiatible polymeric matrix having a soluble TNFα receptor incorporated therein, wherein said receptor is incorporated in said polymeric material in such a manner as to permit the controlled release of an amount of soluble TNFα receptor effective to ameliorate the deleterious effects of TNFα.

2. A pharmaceutical composition according to claim 1, wherein said polymeric matrix is a biocompatible polymer selected from the group consisting of ethylene-vinyl acetate copolymers (EVAc), silicone rubbers, polysaccharides, polyamides, polyacrylates, polyethylenes, polyurethanes, polyisobutylene, and polyphosphazenes.

3. A pharmaceutical composition according to claim 1, wherein said polymeric matrix is a biocompatible polymer selected from the group consisting of polyesters, polyanhydrides, polyorthoesters, polycaprolactone, pseudopolyaminoacids, polypeptides, gelatin, polylactic acid, polyglycolic acid and poly(lactic-glycolic acid) copolymers (PLGA).

4. A pharmaceutical composition according to claim 2, wherein the polymer is polyethylene-vinyl acetate.

5. A pharmaceutical composition according to claim 3, wherein the polymer is poly(lactic-glycolic acid).

6. A pharmaceutical composition according to claim 1, wherein the soluble TNFα receptor is the soluble p55 TNFα receptor (p55 sTNF-R).

7. A pharmaceutical composition according to claim 1, wherein the soluble TNFα receptor is the soluble p75 TNFα receptor (p75 sTNF-R).

8. A pharmaceutical composition according to claim 1, for the treatment of septic shock.

9. A pharmaceutical composition according to claim 1, for the treatment of cancer-associated cachexia.

10. A pharmaceutical composition according to claim 1, for the treatment of autoimmune diseases.

11. A pharmaceutical composition according to claim 10, for the treatment of rheumatoid arthritis.

12. A pharmaceutical composition according to claim 11, further comprising an anti-inflammatory agent.

13. A pharmaceutical composition according to claim 10, for the treatment of multiple sclerosis.

14. A pharmaceutical composition according to claim 13, comprising a further agent for the treatment of multiple sclerosis.

15. A pharmaceutical composition according to claim 10, for the treatment of systemic lupus erythematosus.

16. A pharmaceutical composition according to claim 1, for the treatment of graft-versus-host reaction.

17. A pharmaceutical composition according to claim 1, for the treatment of skin delayed-type hypersensitivity disorders.

18. A pharmaceutical composition according to claim 4, in the form of implant.

19. A pharmaceutical composition according to claim 5, in the form of implant.

20. A pharmaceutical composition according to claim 5, in the form of injection.

21. A pharmaceutical composition according to claim 18, for local injection into the synovial fluid for the treatment of joint inflammation in rheumatoid arthritis.

22. A pharmaceutical composition according to 18, for intrathecal injection into the cerebrospinal fluid for treatment of multiple sclerosis.

23. A pharmaceutical composition according to claim 17, for topical application.

24. A pharmaceutical composition according to claim 14, wherein said further agent is beta interferon or Copolymer-1.

25. A method for the treatment of disorders in which amelioration of the deleterious effects of TNFα is required, comprising administering a controlled release pharmaceutical composition in accordance with claim 1 designed so as to release an effective amount of said soluble form of TNFα receptor, in a manner such that a controlled effective amount is released over time.

26. A method in accordance with claim 25, wherein said disorder is selected from the group consisting of septic shock, cancer-associated cachexia, an autoimmune disease, graft-versus-host reaction and skin delayed-type hypersensitivity disorders.

27. A method in accordance with claim 25, wherein said administering step comprises implanting said controlled release pharmaceutical composition.

28. A pharmaceutical composition for stabilizing the beneficial effects of Tumor Necrosis Factor-α (TNFα), comprising a biocompatible polymeric matrix having therein a complex of soluble TNFα receptor and TNFα, wherein said complex is incorporated in said polymeric matrix in such a manner as to cause the controlled release of an amount of said complex effective to provide the beneficial effects of TNFα.

29. A method according to claim 28, for the treatment of viral, bacterial and multicellular parasiticidal infections.

30. A pharmaceutical composition in accordance with claim 28, wherein said soluble TNFα receptor and said TNFα are present in said complex in a ratio of 1:1.

31. A method for the treatment of tumors, comprising administering a controlled release pharmaceutical composition in accordance with claim 28 designed to release a tumor treatment effective amount of the complex of the soluble form of TNF-α receptor and TNF-α, in a manner such that a controlled effective amount is released over time.

32. A method for the treatment of a disorder requiring the beneficial effects of TNFα, comprising administering a controlled release pharmaceutical composition in accordance with claim 28 designed so as to release an effective amount of the complex or the soluble form of TNFα receptor, and TNFα in a manner such that a controlled effective amount is released over time.

33. A method according to claim 32, for use in wound healing.

34. A method according to claim 32 for the treatment of tumors, wherein said composition is administered at the tumor site.

* * * * *